(12) United States Patent
Kshirsagar et al.

(10) Patent No.: US 11,391,732 B2
(45) Date of Patent: Jul. 19, 2022

(54) MICROORGANISM CONCENTRATION PROCESS

(71) Applicant: 3M INNOVATIVE PROPERTIES COMPANY, St. Paul, MN (US)

(72) Inventors: Manjiri T. Kshirsagar, Woodbury, MN (US); Tushar A. Kshirsagar, Woodbury, MN (US); Thomas E. Wood, Stillwater, MN (US)

(73) Assignee: 3MInnovative Properties Company, St. Paul, MN (US)

( * ) Notice: Subject to any disclaimer, the term of this patent is extended or adjusted under 35 U.S.C. 154(b) by 925 days.

(21) Appl. No.: 15/450,085

(22) Filed: Mar. 6, 2017

(65) Prior Publication Data

US 2017/0176426 A1 Jun. 22, 2017

Related U.S. Application Data

(62) Division of application No. 12/678,362, filed as application No. PCT/US2008/078587 on Oct. 2, 2008, now Pat. No. 9,624,464.

(60) Provisional application No. 60/977,180, filed on Oct. 3, 2007.

(51) Int. Cl.

| | | |
|---|---|---|
| *G01N 33/552* | (2006.01) | |
| *G01N 33/543* | (2006.01) | |
| *C12N 11/14* | (2006.01) | |
| *C12Q 1/04* | (2006.01) | |
| *C12Q 1/24* | (2006.01) | |
| *C01B 33/22* | (2006.01) | |
| *C12N 1/02* | (2006.01) | |
| *G01N 33/553* | (2006.01) | |

(52) U.S. Cl.
CPC ....... *G01N 33/54313* (2013.01); *C01B 33/22* (2013.01); *C12N 1/02* (2013.01); *C12N 11/14* (2013.01); *C12Q 1/04* (2013.01); *C12Q 1/24* (2013.01); *G01N 33/552* (2013.01); *G01N 33/553* (2013.01); *C12Q 1/045* (2013.01)

(58) Field of Classification Search
CPC ........... G01N 33/54313; G01N 33/552; G01N 33/553; G01N 33/551; G01N 33/50; C12N 11/14; C12N 11/00; C12Q 1/04; C12Q 1/24; C01B 33/26; C01B 33/20; C01B 33/22; C01B 33/24; C01B 33/2807; C01B 33/28; C01B 33/32
See application file for complete search history.

(56) References Cited

U.S. PATENT DOCUMENTS

| | | | |
|---|---|---|---|
| 3,912,593 A | 10/1975 | Barker et al. | |
| 4,046,712 A | 9/1977 | Cairns et al. | |
| 4,560,660 A | 12/1985 | Geirnaert | |
| 4,618,525 A | 10/1986 | Chamberlain et al. | |
| 4,698,317 A | 10/1987 | Inoue et al. | |
| 4,729,846 A | 3/1988 | Matsui et al. | |
| 4,838,429 A * | 6/1989 | Fabisiewicz | B65D 75/5838 383/205 |
| 5,071,676 A * | 12/1991 | Jacobson | C09C 1/00 252/520.1 |
| 5,143,878 A | 9/1992 | Dai et al. | |
| 5,238,812 A | 8/1993 | Coulter et al. | |
| 5,364,766 A | 11/1994 | Mach et al. | |
| 5,462,860 A | 10/1995 | Mach | |
| 5,576,185 A | 11/1996 | Coulter et al. | |
| 5,759,403 A | 6/1998 | Clauss et al. | |
| 6,036,679 A * | 3/2000 | Balzar | A61F 13/5514 604/387 |
| 6,045,913 A | 4/2000 | Castle | |
| 6,057,488 A | 5/2000 | Koper et al. | |
| 6,150,300 A | 11/2000 | Khare | |
| 6,254,845 B1 * | 7/2001 | Ohashi | B01J 20/16 423/326 |
| 6,730,230 B2 | 5/2004 | Cook et al. | |
| 6,764,969 B1 | 7/2004 | Kuhn et al. | |
| 6,861,002 B2 | 3/2005 | Hughes | |
| 7,074,916 B2 | 7/2006 | Bastian et al. | |
| 7,201,841 B2 | 4/2007 | Hughes | |
| 7,422,868 B2 | 9/2008 | Fan et al. | |
| 7,431,904 B2 | 10/2008 | Høj | |
| 2002/0077249 A1 | 6/2002 | Schlegel et al. | |

(Continued)

FOREIGN PATENT DOCUMENTS

| | | |
|---|---|---|
| CA | 2056167 | 11/1991 |
| EP | 0093027 | 11/1983 |

(Continued)

OTHER PUBLICATIONS

Masuda-Nishimura et al. Letters in Applied Microbiology 2000, 30, 130-135.*

Feng et al., Trans. Nonferrous Met. Soc. China, 2009, 19:228-234. (Year: 2009).*

Printout of Serpentinite—Wikipedia, downloaded on Apr. 29, 2022 from the website: https://en.wikipedia.org/wiki/Serpentinite (Year: 2022).*

Ams et al., "Experimental measurements of the adsorption of Bacillus subtilis and Pseudomonas mendocina onto Fe-oxyhydroxide-coated and uncoated quartz grains" Geomicrobiology Journal, vol. 21, No. 8, pp. 511-519, ISSN: 0149-0451, XP008100501, Dec. 2004.

(Continued)

*Primary Examiner* — Allison M Fox
*Assistant Examiner* — Qing Xu
(74) *Attorney, Agent, or Firm* — Adrian L. Pishko

(57) ABSTRACT

A process for capturing or concentrating microorganisms for detection or assay comprises (a) providing a concentration agent that comprises an amorphous metal silicate and that has a surface composition having a metal atom to silicon atom ratio of less than or equal to about 0.5, as determined by X-ray photoelectron spectroscopy (XPS); (b) providing a sample comprising at least one microorganism strain; and (c) contacting the concentration agent with the sample such that at least a portion of the at least one microorganism strain is bound to or captured by the concentration agent.

12 Claims, No Drawings

(56) References Cited

U.S. PATENT DOCUMENTS

| | | |
|---|---|---|
| 2003/0009014 A1 | 1/2003 | Chiou |
| 2003/0226443 A1 | 12/2003 | Rajagopalan et al. |
| 2004/0159605 A1 | 8/2004 | Hughes |
| 2004/0178142 A1 | 9/2004 | Koslow |
| 2004/0217061 A1 | 11/2004 | Corzani et al. |
| 2005/0020449 A1 | 1/2005 | Blais |
| 2005/0095189 A1 | 5/2005 | Brey et al. |
| 2006/0024776 A1 | 2/2006 | McMillian |
| 2006/0144793 A1 | 7/2006 | Dadachov |
| 2006/0188580 A1 | 8/2006 | Sacks |
| 2006/0249465 A1 | 11/2006 | Jin et al. |
| 2006/0280801 A1* | 12/2006 | Kronenthal .......... A61K 9/0024 424/489 |
| 2006/0292555 A1 | 12/2006 | Xu et al. |
| 2007/0020649 A1 | 1/2007 | Tseng et al. |
| 2008/0166792 A1 | 7/2008 | Attar et al. |
| 2010/0190171 A1 | 7/2010 | Kshirsagar et al. |
| 2010/0209961 A1 | 8/2010 | Kshirsagar et al. |
| 2010/0247592 A1 | 9/2010 | Kshirsagar et al. |
| 2010/0248214 A1 | 9/2010 | Kshirsagar et al. |

FOREIGN PATENT DOCUMENTS

| | | |
|---|---|---|
| EP | 0391608 | 3/1990 |
| EP | 1524024 | 2/2010 |
| GB | 2228477 | 8/1990 |
| JP | 02-225314 | 9/1990 |
| JP | 03-251179 | 11/1991 |
| JP | H03251179 | * 11/1991 |
| JP | 6-081595 | 10/1994 |
| JP | 9-285287 | 4/1996 |
| JP | 2000-014380 | 1/2000 |
| JP | 2001-112497 | 4/2001 |
| JP | 2002-125695 | 5/2002 |
| JP | 2003-210158 | 7/2003 |
| JP | 2005-254123 | 9/2005 |
| WO | WO 2002/49684 | 6/2002 |
| WO | WO 2003/064330 | 8/2003 |
| WO | WO 2004/011435 | 2/2004 |
| WO | WO 2004/068511 | 8/2004 |
| WO | WO 2004/101435 | 11/2004 |
| WO | WO 2005/030382 | 4/2005 |
| WO | WO 2006/069712 | 7/2006 |
| WO | WO 2006/072944 | 7/2006 |
| WO | WO 2006/074126 | 7/2006 |
| WO | WO 2006/077020 | 7/2006 |
| WO | WO 2006/090375 | 8/2006 |
| WO | WO 2006/128187 | 11/2006 |
| WO | WO 2008/079800 | 7/2008 |
| WO | WO 2009/026035 | 2/2009 |

OTHER PUBLICATIONS

Berry, E. and Siragusa, G. "Hydroxyapatite Adherence as a Means to Concentrate Bacteria" Applied and Environmental Microbiology, pp. 4069-4074, Oct. 1997.

Brown et al., "Virus Removal by Diatomaceous-Earth Filtration—Part 1", Journal American Water Works Association, Denver, CO, vol. 66, No. 2, pp. 98-102, XP001013356, ISSN: 0003-150X, Jan. 1, 1974.

Chaudhuri et al., "Virus Removal by Diatomaceous Earth Filtration", Journal of Environmental Engineering Division, American Society of Civil Engineers, New York, NY, vol. 100, pp. 937-953, XP001013190, ISSN: 0090-3914, Aug. 1, 1974.

Collins et al., "Development of a rapid detection method for waterborne *Escherichia coli* 0157:H7." XP002510684 Database accession No. PREV200300556872 abstract & Abstracts of the General Meeting of the American Society for Microbiology, vol. 103, 2003, pp. Q-496 URL, 103rd American Society for Microbiology General Meeting; Washington, DC, USA; May 18-22, 2003. ISSN: 1060-2011—Database Biosis [Online], Biosciences Information Service, Philadelphia, PA, US; 2003.

Cullison et al. "Magnetized Carbonyl Iron and Insoluble Zirconium Hydroxide Mixture Facilitates Bacterial Concentration and Separation from Nonfat Dry Milk", Journal of Food Protection, vol. 65, No. 11, pp. 1806-1810, Jun. 2002.

Farrah et al., "Adsorption of Viruses by Diatomaceous Earth Coated with Metallic Oxides and Metallic Peroxides", Wat. Sci. Tec., vol. 24, No. 2, pp. 235-240, 1991.

Farrah et al., "Adsorption of Viruses to Diatomaceous Earth Modified by In situ Precipitation of Metallic Salts", Department of Microbiology and Cell Science, University of Florida, vol. 34, No. 9, pp. 520-521, Jan. 1, 1988.

Farrah et al., "Use of Modified Diatomaceous Earth for Removal and Recovery of Viruses in Water" Applied and Environmental Microbiology, vol. 57, No. 9, pp. 2502-2506, XP001013212 ISSN: 0099-2240, Sep. 1, 1991.

Fass et al., "Silicates: non-specific adsorbents in purification of water from viruses", Pub Med, NCBI, Dev. Biol. Stand; vol. 46, pp. 91-96; 1980.

Fass et al., "Silicates as Nonspecific Adsorbents of Bacteriophage: a Model for Purification of Water from Viruses", Pub Med, NCBI, Appl. Environ. Microbiol., vol. 39 (1), pp. 227-232; Jan. 1980.

Fu et al. "Anatase $TiO_2$ Nanocomposites for Antimicrobial Coatings", J. Phys. Chem. B, vol. 109, pp. 8889-8898 (2005).

Jiang et al., "Adsorption of Pseudomonoas Putida on Clay Minerals and Iron Oxide" Colloids and Surfaces. B, Biointerfaces, Elsevier, Amsterdam, NL, vol. 54, No. 2, pp. 217-221, XP005858731, ISSN: 0927-7765, Jan. 25, 2007.

Knapp et al., "The Effect of Distribution of Iron-oxyhydroxide Grain Coatings on the Transport of Bacterial Cells in Porous Media", Environmental Geology (Berlin), vol. 33, No. 4, pp. 243-248, XP002510778, ISSN: 0943-0105, Mar. 1998.

Krack et al. "Effect of Growth Phase and Metabolic Activity on the Adhesion of *Escherichia coli* K-12 AB264 to Quartz and Lepidocrocite", Geomicrobiology Journal, vol. 24, No. 3-4, pp. 179-187, XP008100479, ISSN: 0149-0451, 2007.

Lucore et al., "Immobilization with Metal Hydroxides as a Means to Concentrate Food-Borne Bacteria for Detection by Cultural and Molecular Methods", Applied and Environmental Microbiology, vol. 66, No. 5, pp. 1769-1776, May 2000.

Lukasik et al., "Removal of Microorganisms from Water by Columns Containing Sand Coated with Ferric and Aluminum Hydroxides", Wat. Res., vol. 33, No. 3, pp. 769-777, 1999.

Mills et al., "Effect of Solution Ionic Strength and Iron Coatings on Mineral Grains on the Sorption of Bacterial Cells to Quartz Sand", Applied and Environmental Microbiology, vol. 60, No. 9, pp. 3300-3306, XP002510777, ISSN: 0099-2240, 1994.

Rao et al., "Detection of Viruses in Drinking Water by Concentration on Magnetic Iron Oxide", Applied and Environmental Microbiology, vol. 42, No. 3, pp. 421-426, Sep. 1981.

Salopek et al., The Mining-Geological-Petroleum Engineering Bulletin, vol. 4, No. 1, p. 147-151, 1992.

Sattar et al., "Water Research," vol. 13, No. 7, p. 637-643, 1979.

Schindler et al., "Immobilization and Detection of Listeria Monocytogenes", Applied and Environmental Microbiology, vol. 72, No. 6, pp. 4426-4428, Jun. 2006.

Shah et al., "New Horizons in Purification of Liquids", Soil and Water Pollution Monitoring, Protection and Remediation, 3-23, pp. 369-386, 2006.

Stevens, K. and Jaykus, L-A, "Bacterial Separation and concentration from complex sample matrices: A Review" Critical Reviews in Microbiology, 30 (1), pp. 7-24, 2004.

Stevik et al., "Retention and removal of pathogenic bacteria in wastewater percolating through porous media: a review", Water Research 38 (2004) 1355-1367.

Takeuchi et al., "High Dispersion Platinum Catalyst by RF Sputtering," Journal of Catalysis, vol. 83, pp. 477-479, 1983.

Taylor et al., "Effect of Food Matrix and Cell Growth on PCR-Based Detection of *Escherichia coli* 0157:H7 in Ground Beef", Journal of food Protection, vol. 68, No. 2, pp. 225-232, 2005.

Wegmann et al., "Modification of ceramic microfilters with colloidal zirconia to promote the adsorption of viruses from water", Science Direct, Water Research 42, pp. 1726-1734, 2008.

(56) References Cited

OTHER PUBLICATIONS

Bryant, T., "New UD Technology Removes Viruses From Drinking Water", UDaily, Office of Public Relations, University of Delaware, http://www.udel.edu/PR/UDaily/2007/feb/viruses022607.html, Feb. 26, 2007.
International Search Report, PCT/US2008/078587, International Filing Date Oct. 2, 2008.

\* cited by examiner

MICROORGANISM CONCENTRATION PROCESS

CROSS REFERENCE TO RELATED APPLICATIONS

This application is a divisional of U.S. application Ser. No. 12/678,362, filed Mar. 16, 2010, which is a national stage filing under 35 U.S.C. 371 of PCT/US2008/078587, filed Oct. 2, 2008, which claims the priority of U.S. Provisional Application No. 60/977,180 filed Oct. 3, 2007, the contents of which are hereby incorporated by reference in their entireties.

This application claims the priority of U.S. Provisional Application No. 60/977,180 filed Oct. 3, 2007, the contents of which are hereby incorporated by reference.

FIELD

This invention relates to processes for capturing or concentrating microorganisms such that they remain viable for detection or assay. In other aspects, this invention also relates to diagnostic kits for use in carrying out such concentration processes.

BACKGROUND

Food-borne illnesses and hospital-acquired infections resulting from microorganism contamination are a concern in numerous locations all over the world. Thus, it is often desirable or necessary to assay for the presence of bacteria or other microorganisms in various clinical, food, environmental, or other samples, in order to determine the identity and/or the quantity of the microorganisms present.

Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Bacterial samples can be plated or cultured to increase the numbers of the bacteria in the sample to ensure an adequate level for detection, but the culturing step often requires substantial time and therefore can significantly delay the assessment results.

Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications.

Concentration methods that are not strain-specific have also been used (for example, to obtain a more general assessment of the microorganisms present in a sample). After concentration of a mixed population of microorganisms, the presence of particular strains can be determined, if desired, by using strain-specific probes.

Non-specific concentration or capture of microorganisms has been achieved through methods based upon carbohydrate and lectin protein interactions. Chitosan-coated supports have been used as non-specific capture devices, and substances (for example, carbohydrates, vitamins, iron-chelating compounds, and siderophores) that serve as nutrients for microorganisms have also been described as being useful as ligands to provide non-specific capture of microorganisms.

Various inorganic materials (for example, hydroxyapatite and metal hydroxides) have been used to non-specifically bind and concentrate bacteria. Physical concentration methods (for example, filtration, chromatography, centrifugation, and gravitational settling) have also been utilized for non-specific capture, with and/or without the use of inorganic binding agents. Such non-specific concentration methods have varied in speed, cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness.

SUMMARY

Thus, we recognize that there is an urgent need for processes for rapidly detecting pathogenic microorganisms. Such processes will preferably be not only rapid but also low in cost, simple (involving no complex equipment or procedures), and/or effective under a variety of conditions (for example, with varying types of sample matrices, varying bacterial loads, and varying sample volumes).

Briefly, in one aspect, this invention provides a process for non-specifically concentrating the strains of microorganisms (for example, strains of bacteria, fungi, yeasts, protozoans, viruses (including both non-enveloped and enveloped viruses), and bacterial endospores) present in a sample, such that the microorganisms remain viable for the purpose of detection or assay of one or more of the strains. The process comprises (a) providing a concentration agent (preferably, a particulate concentration agent) that comprises an amorphous metal silicate and that has a surface composition having a metal atom to silicon atom ratio of less than or equal to about 0.5, as determined by X-ray photoelectron spectroscopy (XPS) (for example, a spheroidized talc); (b) providing a sample (preferably, in the form of a fluid) comprising at least one microorganism strain; and (c) contacting (preferably, by mixing) the concentration agent with the sample such that at least a portion of the at least one microorganism strain is bound to or captured by the concentration agent. Preferably, the process further comprises detecting the presence of the at least one bound microorganism strain (for example, by culture-based, microscopy/imaging, genetic, bioluminescence-based, or immunologic detection methods) and/or segregating (preferably, by gravitational settling) the resulting microorganism-bound concentration agent. The process can optionally further comprise separating the resulting segregated concentration agent from the sample.

The process of the invention does not target a specific microorganism strain. Rather, it has been discovered that certain relatively inexpensive, inorganic materials can be surprisingly effective in capturing a variety of microorganisms. Such materials can be used to concentrate the microorganism strains present in a sample (for example, a food sample) in a non-strain-specific manner, so that one or more of the microorganism strains (preferably, one or more strains of bacteria) can be more easily and rapidly assayed.

The process of the invention is relatively simple and low in cost (requiring no complex equipment or expensive strain-specific materials) and can be relatively fast (preferred embodiments capturing at least about 70 percent (more preferably, at least about 80 percent; most preferably, at least about 90 percent) of the microorganisms present in a sample in less than about 30 minutes, relative to a corresponding control sample without concentration agent). In addition, the process can be effective with a variety of microorganisms (including pathogens such as both gram positive and gram negative bacteria) and with a variety of samples (different sample matrices and, unlike at least some prior art methods, even samples having low microorganism content and/or large volumes). Thus, at least some embodiments of the process of the invention can meet the above-cited urgent need for low-cost, simple processes for rapidly detecting pathogenic microorganisms under a variety of conditions.

In another aspect, the invention also provides a diagnostic kit for use in carrying out the process of the invention, the kit comprising (a) a concentration agent (preferably, a particulate concentration agent) that comprises a metal silicate and that has a surface composition having a metal atom to silicon atom ratio of less than or equal to about 0.5, as determined by X-ray photoelectron spectroscopy (XPS); (b) a testing container (preferably, a sterile testing container); and (c) instructions for using the concentration agent in carrying out the process of the invention. Preferably, the diagnostic kit further comprises one or more components selected from microorganism culture media, lysis reagents, buffers, bioluminescence detection assay components, genetic detection assay components, and combinations thereof.

DETAILED DESCRIPTION

Definitions

As used in this patent application:

"sample" means a substance or material that is collected (for example, to be analyzed) by a non-cosmetic method (that is, by a method other than by application and/or removal of a composition comprising the above-described concentration agent to a human body);

"sample matrix" means the components of a sample other than microorganisms;

"detection" means the identification of at least a component of a microorganism, which thereby determines that the microorganism is present;

"genetic detection" means the identification of a component of genetic material such as DNA or RNA that is derived from a target microorganism;

"immunologic detection" means the identification of an antigenic material such as a protein or a proteoglycan that is derived from a target microorganism;

"microorganism" means any cell having genetic material suitable for analysis or detection (including, for example, bacteria, yeasts, viruses, and bacterial endospores);

"microorganism strain" means a particular type of microorganism that is distinguishable through a detection method (for example, microorganisms of different genera, of different species within a genera, or of different isolates within a species); and "target microorganism" means any microorganism that is desired to be detected.

Concentration Agent

Concentration agents suitable for use in carrying out the process of the invention include those that comprise a metal silicate and that have a surface composition having a metal atom to silicon atom ratio of less than or equal to about 0.5 (preferably, less than or equal to about 0.4; more preferably, less than or equal to about 0.3; most preferably, less than or equal to about 0.2), as determined by X-ray photoelectron spectroscopy (XPS). Preferably, the surface composition also comprises at least about 10 average atomic percent carbon (more preferably, at least about 12 average atomic percent carbon; most preferably, at least about 14 average atomic percent carbon), as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Preferred surface composition assessment conditions for XPS can include a take-off angle of 90 degrees measured with respect to the sample surface with a solid angle of acceptance of ±10 degrees.

Concentration or capture using the above-described concentration agents is generally not specific to any particular strain, species, or type of microorganism and therefore provides for the concentration of a general population of microorganisms in a sample. Specific strains of microorganisms can then be detected from among the captured microorganism population using any known detection method with strain-specific probes. Thus, the concentration agents can be used for the detection of microbial contaminants or pathogens (particularly food-borne pathogens such as bacteria) in clinical, food, environmental, or other samples.

When dispersed or suspended in water systems, inorganic materials such as metal silicates exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). The concentration agents used in carrying out the process of the invention have zeta potentials that are more negative than that of, for example, a common metal silicate such as ordinary talc. Yet the concentration agents are surprisingly more effective than talc in concentrating microorganisms such as bacteria, the surfaces of which generally tend to be negatively charged. Preferably, the concentration agents have a negative zeta potential at a pH of about 7 (more preferably, a Smoluchowski zeta potential in the range of about −9 millivolts to about −25 millivolts at a pH of about 7; even more preferably, a Smoluchowski zeta potential in the range of about −10 millivolts to about −20 millivolts at a pH of about 7; most preferably, a Smoluchowski zeta potential in the range of about −11 millivolts to about −15 millivolts at a pH of about 7).

Useful metal silicates include amorphous silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form (more preferably, amorphous, spheroidized metal silicates; most preferably, amorphous, spheroidized magnesium silicate). Metal silicates are known and can be chemically synthesized by known methods or obtained through the mining and processing of raw ores that are naturally-occurring.

Amorphous, at least partially fused particulate forms of metal silicates can be prepared by any of the known methods of melting or softening relatively small feed particles (for example, average particle sizes up to about 25 microns) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle), the description of which is incorporated herein by reference). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, as 3M™ Cosmetic Microspheres CM-111, available from 3M Company, St. Paul, Minn.).

In addition to amorphous metal silicates, the concentration agents can further comprise other materials including oxides of metals (for example, iron or titanium), crystalline metal silicates, other crystalline materials, and the like, provided that the concentration agents have the above-described surface compositions. The concentration agents, however, preferably contain essentially no crystalline silica.

In carrying out the process of the invention, the concentration agents can be used in any form that is amenable to sample contact and microorganism capture (for example, in particulate form or applied to a support such as a dipstick, film, filter, tube, well, plate, beads, membrane, or channel of a microfluidic device, or the like). Preferably, the concentration agents are used in particulate form, more preferably comprising microparticles (preferably, microparticles having a particle size in the range of about 1 micrometer (more preferably, about 2 micrometers) to about 100 micrometers (more preferably, about 50 micrometers; even more preferably, about 25 micrometers; most preferably, about 15 micrometers; where any lower limit can be paired with any upper limit of the range).

Sample

The process of the invention can be applied to a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), a laboratory, or an area that has been potentially subjected to bioterrorism. Food processing, handling, and preparation area samples are preferred, as these are often of particular concern in regard to food supply contamination by bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be used directly or can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is a fluid (for example, a liquid, a gas, or a dispersion or suspension of solid or liquid in liquid or gas).

Examples of samples that can be used in carrying out the process of the invention include foods (for example, fresh produce or ready-to-eat lunch or "deli" meats), beverages (for example, juices or carbonated beverages), potable water, and biological fluids (for example, whole blood or a component thereof such as plasma, a platelet-enriched blood fraction, a platelet concentrate, or packed red blood cells; cell preparations (for example, dispersed tissue, bone marrow aspirates, or vertebral body bone marrow); cell suspensions; urine, saliva, and other body fluids; bone marrow; lung fluid; cerebral fluid; wound exudate; wound biopsy samples; ocular fluid; spinal fluid; and the like), as well as lysed preparations, such as cell lysates, which can be formed using known procedures such as the use of lysing buffers, and the like. Preferred samples include foods, beverages, potable water, biological fluids, and combinations thereof (with foods, beverages, potable water, and combinations thereof being more preferred).

Sample volume can vary, depending upon the particular application. For example, when the process of the invention is used for a diagnostic or research application, the volume of the sample can typically be in the microliter range (for example, 10 μL or greater). When the process is used for a food pathogen testing assay or for potable water safety testing, the volume of the sample can typically be in the milliliter to liter range (for example, 100 milliliters to 3 liters). In an industrial application, such as bioprocessing or pharmaceutical formulation, the volume can be tens of thousands of liters.

The process of the invention can isolate microorganisms from a sample in a concentrated state and can also allow the isolation of microorganisms from sample matrix components that can inhibit detection procedures that are to be used. In all of these cases, the process of the invention can be used in addition to, or in replacement of, other methods of microorganism concentration. Thus, optionally, cultures can be grown from samples either before or after carrying out the process of the invention, if additional concentration is desired.

Contacting

The process of the invention can be carried out by any of various known or hereafter-developed methods of providing contact between two materials. For example, the concentration agent can be added to the sample, or the sample can be added to the concentration agent. A dipstick coated with concentration agent can be immersed in a sample solution, a sample solution can be poured onto a film coated with concentration agent, a sample solution can be poured into a tube or well coated with concentration agent, or a sample solution can be passed through a filter (for example, a woven or nonwoven filter) coated with concentration agent.

Preferably, however, the concentration agent and the sample are combined (using any order of addition) in any of a variety of containers (optionally but preferably, a capped, closed, or sealed container; more preferably, a capped test tube, bottle, or jar). Suitable containers for use in carrying out the process of the invention will be determined by the particular sample and can vary widely in size and nature. For example, the container can be small, such as a 10 microliter container (for example, a test tube) or larger, such as a 100 milliliter to 3 liter container (for example, an Erlenmeyer flask or a polypropylene large-mouth bottle). The container, the concentration agent, and any other apparatus or additives that contact the sample directly can be sterilized (for example, by controlled heat, ethylene oxide gas, or radiation) prior to use, in order to reduce or prevent any contamination of the sample that might cause detection errors. The amount of concentration agent that is sufficient to capture or concentrate the microorganisms of a particular sample for successful detection will vary (depending upon, for example, the nature and form of the concentration agent and sample volume) and can be readily determined by one skilled in the art. For example, 10 milligrams of concentration agent per milliliter of sample can be useful for some applications.

If desired, contacting can be effected by passing a particulate concentration agent at least once through a sample (for example, by relying upon gravitational settling over a period of, for example, about 10 minutes). Contact can be enhanced by mixing (for example, by stirring, shaking, or use of a rocking platform) such that the particles of concentration agent repeatedly pass or settle through a substantial portion of the sample. For small volumes on the order of microliters (typically less than 0.5 milliliter), mixing can be rapid such as by vortexing or "nutation," for example as described in U.S. Pat. No. 5,238,812 (Coulter et al.), the description of which is incorporated herein by reference. For larger volumes on the order of greater than or equal to 0.5 milliliters (typically 0.5 milliliter to 3 liters), mixing can be achieved by gently tumbling the particulate concentration agent and the sample in an "end over end" fashion, for example as described in U.S. Pat. No. 5,576,185 (Coulter et al.), the description of which is incorporated herein by reference. Such tumbling can be accomplished, for example, by means of a device configured to hold a test tube or other type of reaction vessel and to slowly rotate the test tube or vessel in an "end over end" manner. Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes).

Thus, in carrying out the process of the invention, mixing (for example, agitation, rocking, or stirring) and/or incubation (for example, at ambient temperature) are optional but preferred, in order to increase microorganism contact with the concentration agent. A preferred contacting method includes both mixing (for example, for about 15 seconds to about 5 minutes) and incubating (for example, for about 3 minutes to about 30 minutes) a microorganism-containing sample (preferably, a fluid) with particulate concentration agent. If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, Triton™ X-100 nonionic surfactant available from Union Carbide Chemicals and Plastics, Houston, Tex.), mechanical abrasion/elution agents (for example, glass beads), and the like) can be included in the combination of concentration agent and sample.

If desired, the concentration agent (alone or in combination with, for example, antimicrobial materials and/or with carrier materials in the form of liquids (for example, water or oils), solids (for example, fabrics, polymers, papers, or inorganic solids), gels, creams, foams, or pastes) can be applied to or rubbed against a non-porous or porous, solid, microorganism-contaminated or microorganism-contaminatable material or surface (for example, for use as a "cleaning" agent). Binders, stabilizers, surfactants, or other property modifiers can be utilized, if desired.

For such use, the concentration agent can be applied to woven or nonwoven fabrics and can be applied to disposable surfaces such as paper, tissues, cotton swabs, as well as to a variety of absorbent and nonabsorbent materials. For example, the concentration agent can be incorporated into cloth or paper carrier materials for use as "cleaning" wipes. The concentration agent can be applied (for example, in the form of wipes or pastes comprising a carrier material) to solid surfaces, for example, in home, day-care, industrial, and hospital settings, for cleansing toys, equipment, medical devices, work surfaces, and the like. When used for cleansing or other purposes, the sample can be simultaneously collected and contacted with the concentration agent in a single step, if desired.

Segregation and/or Separation

Optionally but preferably, the process of the invention further comprises segregation of the resulting microorganism-bound concentration agent. Such segregation preferably can be achieved by relying, at least in part, upon gravitational settling (gravity sedimentation; for example, over a time period of about 5 minutes to about 30 minutes). In some cases, however, it can be desirable to accelerate segregation (for example, by centrifugation or filtration) or to use combinations of any of the segregation methods.

The process of the invention can optionally further comprise separating the resulting microorganism-bound concentration agent and the sample. For fluid samples, this can involve removal or separation of the supernatant that results upon segregation. Separation of the supernatant can be carried out by numerous methods that are well-known in the art (for example, by decanting or siphoning, so as to leave the microorganism-bound concentration agent at the bottom of the container or vessel utilized in carrying out the process).

The process of the invention can be carried out manually (for example, in a batch-wise manner) or can be automated (for example, to enable continuous or semi-continuous processing).

Detection

A variety of microorganisms can be concentrated and, optionally but preferably, detected by using the process of the invention, including, for example, bacteria, fungi, yeasts, protozoans, viruses (including both non-enveloped and enveloped viruses), bacterial endospores (for example, *Bacillus* (including *Bacillus anthracis, Bacillus cereus*, and *Bacillus subtilis*) and *Clostridium* (including *Clostridium botulinum, Clostridium difficile*, and *Clostridium perfringens*)), and the like, and combinations thereof (preferably, bacteria, yeasts, viruses, bacterial endospores, fungi, and combinations thereof; more preferably, bacteria, yeasts, viruses, bacterial endospores, and combinations thereof; even more preferably, bacteria, viruses, bacterials endospores, and combinations thereof; most preferably, gram-negative bacteria, gram-positive bacteria, non-enveloped viruses (for example, norovirus, poliovirus, hepatitis A virus, rhinovirus, and combinations thereof), bacterial endospores, and combinations thereof). The process has utility in the detection of pathogens, which can be important for food safety or for medical, environmental, or anti-terrorism reasons. The process can be particularly useful in the detection of pathogenic bacteria (for example, both gram negative and gram positive bacteria), as well as various yeasts, molds, and mycoplasmas (and combinations of any of these).

Genera of target microorganisms to be detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof. Samples can contain a plurality of microorganism strains, and any one strain can be detected independently of any other strain. Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans, Staphylococcal enterotoxin* ssp, *Bacillus cereus, Bacillus anthracis, Bacillus atrophaeus, Bacillus subtilis, Clostridium perfringens, Clostridium botulinum, Clostridium difficile, Enterobacter sakazakii, Pseudomonas aeruginosa*, and the like, and combinations thereof (preferably, *Staphylococcus aureus, Salmonella enterica, Saccharomyces cerevisiae, Bacillus atrophaeus, Bacillus subtilis, Escherichia coli*, human-infecting non-enveloped enteric viruses for which *Escherichia coli* bacteriophage is a surrogate, and combinations thereof).

Microorganisms that have been captured or bound (for example, by adsorption) by the concentration agent can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process. Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.), the descriptions of which are incorporated herein by reference.

Since the process of the invention is non-strain specific, it provides a general capture system that allows for multiple microorganism strains to be targeted for assay in the same sample. For example, in assaying for contamination of food samples, it can be desired to test for *Listeria monocytogenes, Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

Diagnostic Kit

A diagnostic kit for use in carrying out the process of the invention comprises (a) an above-described concentration agent (preferably, particulate); (b) a testing container (preferably, a sterile testing container); and (c) instructions for using the concentration agent in carrying out the process of the invention. Preferably, the diagnostic kit further comprises one or more components selected from microorganism culture or growth media, lysis reagents, buffers, bioluminescence detection assay components (for example, luminometer, lysis reagents, luciferase enzyme, enzyme substrate, reaction buffers, and the like), genetic detection assay components, and combinations thereof. A preferred lysis reagent is a lytic enzyme supplied in a buffer, and preferred genetic detection assay components include one or more primers specific for a target microorganism.

For example, a preferred embodiment of the diagnostic kit of the invention contains a particulate concentration agent (for example, in a sterile disposable container such as a glass or polypropylene vial), in combination with instructions for using said agent in carrying out the process of the invention (for example, by mixing the concentration agent with a fluid sample to be analyzed, allowing the concentration agent to settle by gravity, removing the resulting supernatant, and detecting the presence of at least one concentration agent-bound target microorganism strain). The concentration agent optionally can be hydrated in a small volume of buffer with preservative to improve stability during storage and transportation and/or can be contained/aliquotted in a tear-open, sealed pouch to prevent contamination. The concentration agent can be in the form of a dispersion or suspension in a liquid or can be in powder form. Preferably, the diagnostic kit comprises pre-measured aliquots (for example, based upon sample volume) of particulate concentration agent (more preferably, contained in one or more tear-open, sealed pouches).

EXAMPLES

Objects and advantages of this invention are further illustrated by the following examples, but the particular materials and amounts thereof recited in these examples, as well as other conditions and details, should not be construed to unduly limit this invention.

Materials

Crystalline magnesium silicate concentration agent (hereinafter, Talc) was purchased from Mallinckrodt Baker, Inc. (Phillipsburg, N.J.). All microorganism cultures were purchased from The American Type Culture Collection (ATCC; Manassas, Va.).

Amorphous, spheroidized magnesium silicate concentration agent (hereinafter, AS-Talc) was obtained as 3M™ Cosmetic Microspheres CM-111 (shaped as solid spheres; particle density of 2.3 g/cubic centimeter; surface area of 3.3 $m^2/g$; particle size: 90 percent less than about 11 microns, 50 percent less than about 5 microns, 10 percent less than about 2 microns; available from 3M Company, St. Paul, Minn.).

Zeta Potential Measurements

Zeta potentials of aqueous dispersions of the Talc and AS-Talc concentration agents (5.75 weight percent Talc and 5.8 weight percent AS-Talc, respectively, in 18 mega ohms deionized water obtained by using a Milli-Q™ Elix 10™ Synthesis A10 deionization system from Millipore Corporation, Bedford, Mass.) were measured as a function of added hydrochloric acid (pH) using a Colloidal Dynamics Acoustosizer II™ multi-frequency electroacoustic spectral analyzer (Colloidal Dynamics, Warwick, R.I.) equipped with a TM200 automatic titration module, pH electrode, and in-line conductivity cell. Measurements were made using polar calibration and polar sample settings with the following general parameters:

Starting Volume: 170 mL of dispersion
Titration Volume: 5 to 10 mL at finish; 20 steps for each titration
Titrant: 1.0 N hydrochloric acid in water
   (J. T. Baker, Phillipsburg, N.J.)
Stir Rate: 300 revolutions per minute (rpm)
Pump Rate: 400 mL per minute
Mixing Delay: 120 seconds with stirring after acid addition before measurement At a pH of about 7, the AS-Talc exhibited a Smoluchowski zeta potential of about −12 mV, and the Talc exhibited a Smoluchowski zeta potential of about −8 mV.

Surface Composition Analysis

The surface compositions of samples of the Talc and AS-Talc concentration agents were analyzed by X-ray photoelectron spectroscopy (XPS; also known as ESCA). Samples of the powders were pressed onto double-sided, pressure sensitive adhesive tapes on aluminum foil. Excess powder was removed from each sample surface by blowing with compressed nitrogen gas.

Spectral data was acquired using a Kratos AXIS Ultra™ DLD spectrometer (Kratos Analytical, Manchester, England) having a monochromatic Al—$K_{60}$ X-ray excitation source (1487 eV) and a hemispherical electron energy analyzer operated in a constant pass energy mode. The emitted photoelectrons were detected at a take-off angle of 90 degrees measured with respect to the sample surface with a solid angle of acceptance of ±10 degrees. A low-energy electron flood gun was used to minimize surface charging. Measurements were made using a 140 Watt power to anode and $2 \times 10^{-8}$ Torr chamber pressure.

An area of the surface of each concentration agent sample measuring about 300 micrometers by about 700 micrometers was analyzed for each data point. Three areas on each sample were analyzed and averaged to obtain the reported average atomic percent values. Data processing was carried out using standard Vision2™ software (Kratos Analytical, Manchester, England). Results (elements present at a detectable level by XPS on the surface of the concentration agents) are shown in Table A below:

TABLE A

| Concentration Agent | Magnesium (Average Atomic Percent) | Silicon (Average Atomic Percent) | Ratio of Magnesium to Silicon | Carbon (Average Atomic Percent) | Oxygen (Average Atomic Percent) |
|---|---|---|---|---|---|
| Talc | 17 | 26 | 0.65 | 6.9 | 50 |
| AS-Talc | 6.5 | 32 | 0.20 | 14 | 47 |

Microorganism Concentration Test Method

An isolated microorganism colony was inoculated into 5 mL BBL™ Trypticase™ Soy Broth (Becton Dickinson, Sparks, Md.) and incubated at 37° C. for 18-20 hours. This overnight culture at ~$10^9$ colony forming units per mL was diluted in adsorption buffer (containing 5 mM KCl, 1 mM $CaCl_2$, 0.1 mM $MgCl_2$, and 1 mM $K_2HPO_4$) at pH 7.2 to obtain $10^3$ microorganisms per mL dilution. A 1.1 mL volume of the microorganism dilution was added to separate, labeled sterile 5 mL polypropylene tubes (BD Falcon™ Becton Dickinson, Franklin Lakes, N.J.) containing 10 mg of concentration agent, each of which was capped and mixed on a Thermolyne Maximix Plus™ vortex mixer (Barnstead International, Iowa). Each capped tube was incubated at room temperature (25° C.) for 15 minutes on a Thermolyne Vari Mix™ shaker platform (Barnstead International, Iowa). After the incubation, each tube was allowed to stand on the lab bench for 10 minutes to settle the concentration agent. Control sample tubes containing 1.1 mL of the microorganism dilution without concentration agent were treated in the same manner. The resulting settled concentration agent and/or supernatant (and the control samples) were then used for analysis.

The settled concentration agent was re-suspended in 1 mL sterile Butterfield's Buffer solution (pH 7.2±0.2; monobasic potassium phosphate buffer solution; VWR Catalog Number 83008-093, VWR, West Chester, Pa.) and plated on 3M™ Petrifilm™ Aerobic Count Plates culture medium (dry, rehydratable; 3M Company, St. Paul, Minn.) according to the manufacturer's instructions. Aerobic count was quantified using a 3M™ Petrifilm™ Plate Reader (3M Company, St. Paul, Minn.). Results were calculated using the following formula:

Percent CFU/mL in Re-suspended Concentration Agent=number of colonies from plated re-suspended concentration agent)/(number of colonies from plated untreated control sample)×100

(where CFU=Colony Forming Unit, which is a unit of live or viable microorganisms). Results were then reported in terms of percent capture of microorganisms by the concentration agent using the formula below:

Capture Efficiency or Percent Capture=Percent CFU/mL in Re-suspended Concentration Agent For comparison purposes, in at least some cases 1 mL of the supernatant was removed and plated undiluted or diluted 1:10 in Butterfield's Buffer solution and plated onto 3M™ Petrifilm™ Aerobic Count Plates culture medium. Aerobic count was quantified using a 3M™ Petrifilm™ Plate Reader (3M Company, St. Paul, Minn.). Results were calculated using the following formula:

Percent CFU/mL in Supernatant=(number of colonies from plated supernatant)/(number of colonies from plated untreated control sample)×100

(where CFU=Colony Forming Unit, which is a unit of live or viable microorganisms). When the microorganism colonies and the concentration agent were similar in color (providing little contrast for the plate reader), results were based upon the supernatant and were then reported in terms of percent capture of microorganisms by the concentration agent using the formula below:

Capture Efficiency or Percent Capture=100−Percent CFU/mL in Supernatant

Examples 1 and 2 and Comparative Examples 1 and 2

Using the above-described microorganism concentration test method, 10 mg amorphous, spheroidized magnesium silicate (prepared as described above; hereinafter, AS-Talc) and crystalline (non-spheroidized) magnesium silicate (hereinafter, Talc) were tested separately for bacterial concentration against target microorganisms, the gram-negative bacterium *Salmonella enterica* subsp.*enterica serovar Typhimurium* (ATCC 35987) and the gram-positive bacterium *Staphylococcus aureus* (ATCC 6538). The results are shown in Table 1 below (standard deviation for all samples less than 10 percent).

TABLE 1

| Example No. | Microorganism | Concentration Agent | Percent Capture |
|---|---|---|---|
| C-1 | *Staphylococcus* | Talc | 58 |
| 1 | *Staphylococcus* | AS-Talc | 99 |
| C-2 | *Salmonella* | Talc | 69 |
| 2 | *Salmonella* | AS-Talc | 92 |

Examples 3-5 and Comparative Examples 3-5

Using the above-described microorganism concentration test method, different weights per unit volume of AS-Talc and Talc were tested separately for bacterial concentration of the target microorganism, *Salmonella enterica* subsp.*enterica serovar Typhimurium* (ATCC 35987). The results are shown in Table 2 below (standard deviation for all samples less than 10 percent).

TABLE 2

| Example No. | Microorganism | Concentration Agent | Amount of Concentration Agent (mg/mL) | Percent Capture |
|---|---|---|---|---|
| C-3 | *Salmonella* | Talc | 1 | 63 |
| 3 | *Salmonella* | AS-Talc | 1 | 82 |
| C-4 | *Salmonella* | Talc | 5 | 64 |
| 4 | *Salmonella* | AS-Talc | 5 | 90 |
| C-5 | *Salmonella* | Talc | 10 | 69 |
| 5 | *Salmonella* | AS-Talc | 10 | 95 |

Examples 6-8 and Comparative Examples 6-8

Using the above-described microorganism concentration test method, 10 mg of AS-Talc and Talc were tested separately against different bacterial concentrations of the target microorganism, *Salmonella enterica* subsp.*enterica serovar Typhimurium* (ATCC 35987). The results are shown in Table 3 below.

TABLE 3

| Example No. | Microorganism | Concentration Agent | Microorganism Concentration (CFU/mL) | Percent Capture ± Standard Deviation |
|---|---|---|---|---|
| C-6 | *Salmonella* | Talc | 10 | 68 ± 9 |
| 6 | *Salmonella* | AS-Talc | 10 | 92 ± 11 |
| C-7 | *Salmonella* | Talc | 100 | 74 ± 3 |
| 7 | *Salmonella* | AS-Talc | 100 | 98 ± 3 |
| C-8 | *Salmonella* | Talc | 1000 | 69 ± 1 |
| 8 | *Salmonella* | AS-Talc | 1000 | 92 ± 1 |

Examples 9-11 and Comparative Examples 9-11

Using the above-described microorganism concentration test method, 10 mg of AS-Talc and Talc were tested separately for bacterial concentration of the target microorganism, *Salmonella enterica* subsp.*enterica serovar Typhimurium* (ATCC 35987) for 5, 10, and 15 minutes of incubation. The results are shown in Table 4 below (standard deviation for all samples less than 10 percent).

TABLE 4

| Example No. | Microorganism | Concentration Agent | Incubation Time (minutes) | Percent Capture |
|---|---|---|---|---|
| C-9 | *Salmonella* | Talc | 5 | 74 |
| 9 | *Salmonella* | AS-Talc | 5 | 97 |
| C-10 | *Salmonella* | Talc | 10 | 77 |
| 10 | *Salmonella* | AS-Talc | 10 | 96 |
| C-11 | *Salmonella* | Talc | 15 | 75 |
| 11 | *Salmonella* | AS-Talc | 15 | 92 |

Example 12 and Comparative Example 12

Using the above-described microorganism concentration test method, with the exception of the use of Butterfield's Buffer solution instead of adsorption buffer, 10 mg of AS-Talc and Talc were tested separately for yeast concentration of the target microorganism, *Saccharomyces cerevisiae* ($10^2$ CFU/mL; ATCC 201390). The resulting materials were plated on 3M™ Petrifilm™ Yeast and Mold Count Plate culture medium (dry, rehydratable; 3M Company, St.

Paul, Minn.) and incubated for 5 days according to the manufacturer's instructions. Isolated yeast colonies were counted manually, and percent capture was calculated as described above. Percent capture was 97 percent for AS-Talc and 82 percent for Talc (standard deviation for all samples less than 10 percent).

Examples 13-15

Food samples were purchased from a local grocery store (Cub Foods, St. Paul). Turkey slices and apple juice (11 g) were weighed in sterile glass dishes and added to sterile Stomacher™ polyethylene filter bags (Seward Corp, Norfolk, UK). The food samples were spiked with bacterial cultures at a $10^2$ CFU/mL concentration using an 18-20 hour overnight culture (stock) of Salmonella enterica subsp.enterica serovar Typhimurium (ATCC 35987). This was followed by the addition of 99 mL of Butterfield's Buffer solution to each spiked sample. The resulting samples were blended for a 2-minute cycle in a Stomacher™ 400 Circulator laboratory blender (Seward Corp. Norfolk, UK). The blended samples were collected in sterile 50 mL centrifuge tubes (BD Falcon™, Becton Dickinson, Franklin Lakes, N.J.) and centrifuged at 2000 revolutions per minute (rpm) for 5 minutes to remove large debris. The resulting supernatants were used as samples for further testing. The pH of the apple juice-based supernatant was adjusted to 7.2 before testing by adding 1N sodium hydroxide (VWR, West Chester, Pa.). Potable water (100 mL) from a drinking fountain was collected in a sterile 250 mL glass bottle (VWR, West Chester, Pa.) and was inoculated with the target microorganism Salmonella enterica subsp.enterica serovar Typhimurium (ATCC 35987) at $10^2$ CFU/mL, mixed manually end-to-end 5 times, and incubated at room temperature (25° C.) for 15 minutes. This water sample was used for further testing.

Using the above-described microorganism concentration test method, each 1 mL test sample prepared as above was added separately to a test tube containing 10 mg of AS-Talc and tested for bacterial concentration of the target microorganism, Salmonella enterica subsp.enterica serovar Typhimurium (ATCC 35987). The results are shown in Table 5 below (standard deviation for all samples less than 10 percent).

TABLE 5

| Example No. | Microorganism | Concentration Agent | Sample | Percent Capture |
|---|---|---|---|---|
| 13 | Salmonella | AS-Talc | Apple Juice | 86 |
| 14 | Salmonella | AS-Talc | Turkey | 78 |
| 15 | Salmonella | AS-Talc | Potable Water | 98 |

Examples 16 and 17

AS-Talc was tested for concentration of the target microorganism Salmonella enterica subsp.enterica serovar Typhimurium (ATCC 35987) from large-volume samples (300 mg AS-Talc per 30 mL sample volume). Potable water (100 mL) from a drinking fountain was collected in a sterile 250 mL glass bottle (VWR, West Chester, Pa.) and inoculated with the target microorganism Salmonella enterica subsp.enterica serovar Typhimurium (ATCC 35987) at $10^2$ CFU/mL. The resulting inoculated water was mixed manually end-to-end 5 times and incubated at room temperature (25° C.) for 15 minutes. 30 mL samples of the incubated water were added to sterile 50 mL conical polypropylene centrifuge tubes (BD Falcon™, Becton Dickinson, Franklin Lakes, N.J.) containing 300 mg of AS-Talc and were tested by using the above-described microorganism concentration test method. The resulting settled AS-Talc was re-suspended in 30 mL sterile Butterfield's Buffer solution, and 1 mL of the resulting suspension was plated on 3M™ Petrifilm™ Aerobic Count Plates culture medium. Percent capture was 98 percent (standard deviation less than 10 percent).

Whole grape tomatoes (11 g) from a local grocery store (Cub Foods, St. Paul) were placed in a sterile petridish and were inoculated with the target microorganism Salmonella enterica subsp.enterica serovar Typhimurium (ATCC 35987) at $10^2$ CFU/mL, mixed manually by swirling 5 times, and incubated at room temperature (25° C.) for 5 minutes. The tomatoes were added to sterile Stomacher™ polyethylene filter bags (Seward Corp, Norfolk, UK) containing 99 mL of Butterfield's Buffer solution. The contents of the bags were mixed by swirling for 1 minute. 30 mL samples were added to sterile 50 mL conical polypropylene centrifuge tubes (BD Falcon™, Becton Dickinson, Franklin Lakes, N.J.) containing 300 mg of AS-Talc and tested for bacterial concentration using the above-described microorganism concentration test method. The AS-Talc particles were settled by centrifugation at 2000 rpm for 5 minutes (Eppendorf, Westbury, N.Y.). The settled particles were re-suspended in 30 mL sterile Butterfield's Buffer solution, and 1 mL of the resulting suspension was plated on 3M™ Petrifilm™ Aerobic Count Plates culture medium. Percent capture was 99 percent (standard deviation less than 10 percent).

Examples 18 and 19

10 mg of AS-Talc was tested for concentration of the target bacterial endospores Bacillus atrophaeus (ATCC 9372) and Bacillus subtilis (ATCC 19659). The above-described microorganism concentration test method was utilized with the following modifications: the overnight cultures had $2\times10^2$ CFU/mL Bacillus atrophaeus and $7\times10^2$ CFU/mL Bacillus subtilis, respectively; the resulting supernatants were plated undiluted; the settled concentration agent with bound Bacillus atrophaeus was resuspended in 1 mL sterile Butterfield's Buffer solution and plated; and the settled concentration agent with bound Bacillus subtilis was resuspended in 5 mL sterile Butterfield's Buffer solution and plated (1 mL each). Capture efficiencies were calculated based on counts from the plated supernatants, and the results are shown in Table 6 below (standard deviation for all samples less than 10 percent).

TABLE 6

| Example No. | Microorganism | Concentration Agent | Percent Capture |
|---|---|---|---|
| 18 | Bacillus atrophaeus | AS-Talc | 97 |
| 19 | Bacillus subtilis | AS-Talc | 95 |

Examples 20 and 21

10 mg of AS-Talc was tested for concentration of the target non-enveloped, bacteria-infecting virus, Escherichia coli bacteriophage MS2 (ATCC 15597-B1; which is often used as a surrogate for various human-infecting, non-enveloped enteric viruses). A double layer agar method (described below) was used to assay for capture of the *Escherichia coli* bacteriophage MS2 (ATCC 15597-B1) using *Escherichia coli* bacteria (ATCC 15597) as host.

*Escherichia coli* bacteriophage MS2 stock was diluted ten-fold serially in sterile 1× adsorption buffer (containing 5 mM KCl, 1 mM $CaCl_2$, 0.1 mM $MgCl_2$, and 1 mM $K_2HPO_4$) at pH 7.2 to obtain two dilutions with $10^3$ and $10^2$ plaque forming units per milliliter (PFUs/mL), respectively. A 1.0 mL volume of resulting bacteriophage dilution was added to a labeled sterile 5 mL polypropylene tube (BD Falcon™, Becton Dickinson, Franklin Lakes, N.J.) containing 10 mg of concentration agent and mixed on a Thermolyne Maximix Plus™ vortex mixer (Barnstead International, Iowa). The capped tube was incubated at room temperature (25° C.) for 15 minutes on a Thermolyne Vari Mix™ shaker platform (Barnstead International, Iowa). After the incubation, the tube was allowed to stand on the lab bench for 10 minutes to settle the concentration agent. A control sample tube containing 1.0 mL of the bacteriophage dilution without concentration agent was treated in the same manner. The resulting settled concentration agent and supernatant (and the control sample) were then used for analysis.

100 microliters of the supernatant was removed and assayed for bacteriophage using the double layer agar method described below. An additional 800 microliters of supernatant was removed and discarded. One hundred microliters of the settled concentration agent was also assayed for bacteriophage.

Double Layer Agar Method:

A single colony of *Escherichia coli* bacteria (ATCC 15597) was inoculated into 25 mL sterile 3 weight percent tryptic soy broth (Bacto™ Tryptic Soy Broth, Becton Dickinson and Company, Sparks, Md.; prepared according to manufacturer's instructions) and incubated at 37° C. in a shaker incubator (Innova™ 44, New Brunswick Scientific Co., Inc., Edison, N.J.) set at 250 revolutions per minute (rpm) overnight. 750 microliters of this overnight culture was used to inoculate 75 mL sterile 3 weight percent tryptic soy broth. The resulting culture was incubated at 37° C. in the shaker incubator set at 250 rpm to obtain *Escherichia coli* cells in the exponential phase as measured by absorbance at 550 nm (absorbance values 0.3-0.6) using a SpectraMax M5 spectrophotometer (Molecular Devices, Sunnyvale, Calif.). The cells were incubated on ice until used for assay.

One hundred microliters of the above-described bacteriophage test samples were mixed with 75 microliters of the ice-incubated *Escherichia coli* (host bacteria) cells and incubated at room temperature (25° C.) for 5 minutes. The resulting samples were mixed with 5 mL sterile molten top agar (3 weight percent tryptic soy broth, 1.5 weight percent NaCl, 0.6 weight percent agar; prepared that day and maintained in a 48° C. waterbath). The mixture was then poured on top of bottom agar (3 weight percent tryptic soy broth, 1.5 weight percent NaCl, weight percent agar) in petridishes. The molten agar component of the mixture was allowed to solidify for 5 minutes, and the petridishes or plates were inverted and incubated at 37° C. The plates were visually inspected after overnight incubation, and those plates containing settled concentration agent (as well as the control plate) showed the presence of bacteriophage plaques. Capture efficiencies were calculated based on counts from the plated supernatants and determined to be 72 percent for the $10^2$ PFU/mL dilution (standard deviation less than 10 percent).

Example 22

Apple juice was purchased from a local grocery store (Cub Foods, St. Paul). Apple juice (11 g) was weighed in a sterile glass dish and added to 99 mL sterile Butterfield's Buffer. The resulting combination was mixed by swirling for 1 minute and was spiked with two bacterial cultures, each at a 1 CFU/mL concentration, using 18-20 hour overnight cultures (bacterial stocks) of *Salmonella enterica* subsp.*enterica serovar Typhimurium* (ATCC 35987) and *Escherichia coli* (ATCC 51813). Serial dilutions of the bacterial stocks had been made in 1× adsorption buffer as described above.

Using the above-described microorganism concentration test method, a 10 mL volume of the spiked apple juice sample was added to a sterile 50 mL conical polypropylene centrifuge tube (BD Falcon™, Becton Dickinson, Franklin Lakes, N.J.) containing 100 mg of AS-Talc and incubated for 15 minutes for bacterial capture/concentration of the target microorganism, *Salmonella* (in the presence of the *Escherichia coli*, a competitor microorganism). The resulting supernatant was removed, and the settled concentration agent was transferred to another sterile 50 mL tube containing 2 mL sterile 3 weight percent tryptic soy broth (Bacto™ Tryptic Soy Broth, Becton Dickinson and Company, Sparks, Md.; prepared according to manufacturer's instructions). The tube was loosely capped, and its contents were mixed and incubated at 37° C. After overnight incubation, the resulting broth mixture was tested for the presence of *Salmonella* using a RapidChek™ *Salmonella* lateral flow immunoassay test strip from SDI (Strategic Diagnostics, Inc., Newark, Del.). Visual inspection of the test strip showed it to be positive for *Salmonella*.

Nucleic acid detection by polymerase chain reaction (PCR) was also carried out for the microorganism-containing broth mixture. 1 mL of the above-described overnight-incubated, concentration agent-containing broth was assayed as a test sample for the presence of *Salmonella* by using a TaqMan™ ABI *Salmonella enterica* Detection Kit from Applied Biosystems (Foster City, Calif.). As a control sample, 1 mL of the 18-20 hour overnight culture (stock) of *Salmonella enterica* subsp.*enterica serovar Typhimurium* (ATCC 35987) was also assayed. PCR testing was conducted in a Stratagene Mx3005P™ QPCR (quantitative PCR) System (Stratagene Corporation, La Jolla, Calif.) by using the following cycle conditions per cycle for 45 cycles: 25° C. for 30 seconds, 95° C. for 10 minutes, 95° C. for 15 seconds, and 60° C. for 1 minute. An average (n=2) cycle threshold value (CT value) of 17.71 was obtained for the control sample. An average (n=2) CT value of 19.88 was obtained for the test sample containing concentration agent, indicating a positive PCR reaction and confirming the presence of *Salmonella*.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A kit comprising (a) a concentration agent that comprises an amorphous, spheroidized metal silicate and that has a surface composition having a metal atom to silicon atom ratio of less than or equal to 0.5, as determined by X-ray photoelectron spectroscopy (XPS), wherein said concentration agent has a negative zeta potential at a pH of 7, wherein said amorphous, spheroidized metal silicate is in at least partially fused particulate form and wherein said metal silicate is magnesium silicate; (b) a testing container; (c) at least one component selected from microorganism culture media, lysis reagents, buffers, bioluminescence detection assay components, genetic detection assay components, and combinations thereof, and (d) instructions for using said concentration agent in a process to bind or capture at least one microorganism strain.

2. The kit of claim 1, wherein said concentration agent is in particulate form, said testing container is sterile and disposable, and said testing container contains said concentration agent.

3. The kit of claim 1, wherein said kit comprises at least one pre-measured aliquot of said concentration agent in particulate form in at least one tear-open, sealed pouch.

4. The kit of claim 1, wherein said surface composition has a metal atom to silicon atom ratio of less than or equal to 0.4.

5. The kit of claim 1, wherein said concentration agent is formed from melted or softened silicate feed particles.

6. The kit of claim 1, wherein said at least one component is selected from said microorganism culture media.

7. The kit of claim 1, wherein said at least one component is selected from said lysis reagents.

8. The kit of claim 1, wherein said at least one component is selected from said bioluminescence detection assay components, genetic detection assay components, and combinations thereof.

9. The kit of claim 1, wherein said at least one component is selected from said buffers.

10. The kit of claim 1, wherein said concentration agent comprises microparticles having a particle size in the range of about 1 micrometer to about 100 micrometers.

11. The kit of claim 1, wherein said concentration agent is in the form of a dispersion or a suspension in a liquid.

12. The kit of claim 1, wherein said concentration agent has a zeta potential in the range of about −9 millivolts to about −25 millivolts at a pH of 7.

* * * * *